United States Patent
Nakamura et al.

(10) Patent No.: US 6,316,447 B1
(45) Date of Patent: Nov. 13, 2001

(54) PESTICIDAL COMPOSITION

(75) Inventors: Satoshi Nakamura, Takarazuka; Makoto Hatakoshi, Toyonaka, both of (JP); Robert Senn, Witterswil; Daniele Fuog, Arzo, both of (CH); Tümay Tekin, Adana-Turkey (TK)

(73) Assignees: Syngenta Crop Protection, Inc., Greensboro, NC (US); Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/403,465

(22) PCT Filed: Apr. 20, 1998

(86) PCT No.: PCT/EP98/02395

§ 371 Date: Jan. 12, 2000

§ 102(e) Date: Jan. 12, 2000

(87) PCT Pub. No.: WO98/47368

PCT Pub. Date: Oct. 29, 1998

(30) Foreign Application Priority Data

Apr. 22, 1997 (CH) ............................................ 929/97

(51) Int. Cl.[7] ............................ A01N 43/64; A01N 43/40
(52) U.S. Cl. ........................................... 514/242; 514/345
(58) Field of Search ......................... 514/242, 345

(56) References Cited

FOREIGN PATENT DOCUMENTS 2 720 230    12/1995   (FR) .

OTHER PUBLICATIONS

The Pesticide Manual, 11th Ed. (1995), pp. 887–888 and 1339, XP–002075650.
CA 117:21926 (of JP 03 220 177), XP–002075651 (1991).
Proc. Br. Crop. Prot. Conf. Pests Dis. (1, 75–80, 1996), Abstract, XP–002075652.
Derwent Abstract 96–032163/199604 (of FR 2 720 230) (1995).

Primary Examiner—Allen J. Robinson
(74) Attorney, Agent, or Firm—William A. Teoli, Jr.

(57) ABSTRACT

There are described a pesticidal composition which comprises, in variable quantities, the pesticidally active compound of the formula

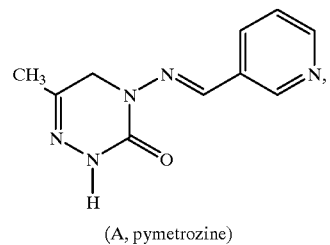

(A, pymetrozine)

in free form or in the form of an agrochemically acceptable salt,
and the pesticidally active compound of the formula

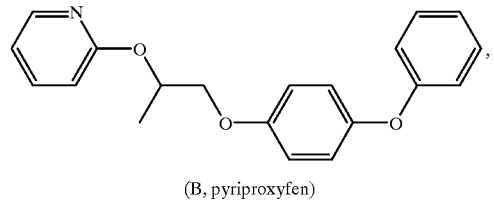

(B, pyriproxyfen)

in free form or in the form of an agrochemically acceptable salt,
and at least one auxiliary,
a combination of the active ingredients (A) and (B), a method of controlling pests, a process for the preparation of the composition, its use, plant propagation material treated with the composition, and the use of the compound of the formula (A) and the use of the compound of the formula (B) for the preparation of the composition.

8 Claims, No Drawings

PESTICIDAL COMPOSITION

This application is a 371 of PCT/EP98/02395, filed Apr. 20, 1998.

The present invention relates to a pesticide which comprises a pesticidally active combination of active ingredients, a method of controlling pests using this composition, a process for the preparation of the composition, its use, plant propagation material treated with the composition, and to the use of a compound of the formulae (A) and (B) below for the preparation of the composition.

Certain mixtures of active ingredients are proposed in the literature for the purposes of pest control. However, the biological properties of these known mixtures are not fully satisfactory in the field of pest control, which is why there is a need to provide other mixtures, especially those which have synergistic properties, for example synergistic pesticidal properties, in particular for controlling insects and representatives of the order Acarina. This object is achieved in accordance with the invention by providing the present composition.

The invention relates to a pesticidal composition which comprises, in variable quantities, the pesticidally active compound of the formula

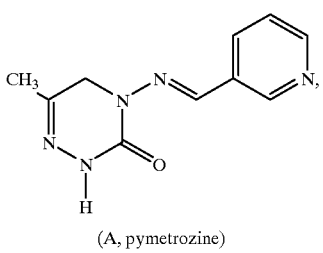

(A, pymetrozine)

in free form or in the form of an agrochemically acceptable salt,
and the pesticidally active compound of the formula

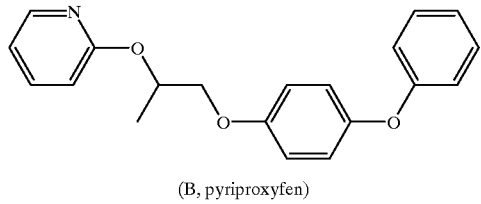

(B, pyriproxyfen)

in free form or in the form of an agrochemically acceptable salt, and at least one auxiliary.

The compound (E)-4,5-dihydro-6-methyl-4-(3-pyridylmethyleneamino)-1,2,4-triazin-3(2H)one (pymetrozine) of the formula (A), is known, for example, from The Pesticide Manual, 10$^{th}$Ed. (1994). The British Crop Protection Council, London, page 868.

The compound 4-phenoxyphenyl (RS)-2-(2-pyridyloxy) propyl ether(pyriproxyfen) is known from The Pesticide Manual, 10$^{th}$ Ed. (1994). The British Crop Protection Council, London, page 887.

The agrochemically acceptable salts of the compounds of the formulae (A) and (B) are, for example, acid addition salts of inorganic and organic acids, in particular of hydrochloric acid, hydrobromic acid, sulfuric acid, nitric acid, perchloric acid, phosphoric acid, formic acid, acetic acid, trifluoroacetic acid, oxalic acid, malonic acid, toluenesulfonic acid or benzoic acid.

Preferred within the scope of the present invention are compositions which comprise, as active ingredients, the compounds of the formulae (A) and (B) in free form.

The active ingredient combination according to the invention comprises the active ingredient of the formula (A) and the active ingredient of the formula (B) preferably in a mixing ratio (weight ratio, molar weight ratio or ratio of the $LD_{50}$ values of the pests to be controlled in each case) of from 1:200 to 200:1, in particular 1:50 to 50:1, more particularly in a ratio of between 1:20 and 20:1, especially between 10:1 and 1:10, also preferably between 50:1 and 3:1, very especially between 40:1 and 10:1, also preferably between 2:1 and 1:2, on the other hand in a ratio of 150:1, 40:1 or 30:1, or 20:1, or 20:3, or 15:1, or 10:1, or 5:1, or 5:2, or 5:3, or 5:4, or 4:1, or 4:3, or 3:1, or 3:2, or 2:1, or 1:20, or 1:10, or 1:5, or 2:5, or 3:5, or 4:5, or 1:4, or 3:4, or 1:3, or 2:3, or 1:2, or 1:1.

The invention also relates to a combination, in variable quantities, of the pesticidally active compound of the formula (A), in free form or in the form of an agrochemically acceptable salt, with the pesticidally active compound of the formula (B), in free form or in the form of an agrochemically acceptable salt.

Surprisingly, it has now been found that the combination of the active ingredient of the formula (A) with the active ingredient of the formula (B) not only causes the additive supplementation of the biocidal and the physical properties to be expected in principle, but that it generates a synergistic effect which, inter alia, widens the range of the pesticidal activity of the two compounds.'

Surprisingly, it has now been found that, in particular, for example the pesticidal activity of the compositions according to the invention is not only additive in comparison with the pesticidal activities of the individual components (A) and (B), as can essentially be expected, but that a synergistic effect is present. The term "synergistic" in the present context is however by no means restricted to the pesticidal activity, but the term also relates to other advantageous properties of the compositions according to the invention in comparison with the individual components (A) and (B). Examples of such advantageous properties which may be mentioned are: a widening of the pesticidal spectrum of action to include other pests, for example resistant strains, a reduced rate of application of the compounds of the formulae (A) and (B), sufficient control of the pests with the aid of the compositions according to the invention even at a rate of application at which the individual compounds (A) and (B) are entirely ineffective; advantageous behaviour upon formulation and/or application, for example upon grinding, screening, emulsifying, dissolving or dispersing; improved storage stability; better light stability; more advantageous degradation behaviour; improved toxicological or ecotoxicological behaviour; or other advantages known to those skilled in the art.

The compositions according to the invention are preventively and/or curatively valuable in the field of pest control, even at low rates of concentration, while being well tolerated by warm-blooded species, fish and plants, and have a very advantageous biocidal spectrum. The compositions according to the invention are active against all or some developmental stages of normally sensitive, but also resistant, animal pests such as insects and representatives of the order Acarina. The insecticidal and/or acaricidal activity of the compositions according to the invention can manifest itself directly, i.e. in destruction of the pests, which takes place immediately or only after some time has elapsed, for example during ecdysis, or indirectly, e.g. in a reduced oviposition and/or hatching rate, the good activity corresponding to a destruction rate (mortality) of at least 40 to 50%.

Examples of the abovementioned animal pests are:

from the order Lepidoptera Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta,* Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example, Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Oryzaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example, Blatta spp., Blattella spp., Gryllotalpa spp., *Leucophaea maderae*, Locusta spp., Periplaneta spp. and Schistocerca spp.;

from the order Isoptera, for example, Reticulitermes spp.;

from the order Psocoptera, for example, Liposcelis spp.;

from the order Anoplura, for example, Haematopinus spp., Linognathus spp., Pediculus spp., Pemphigus spp. and Phylloxera spp.;

from the order Mallophaga, for example, Damalinea spp. and Trichodectes spp.;

from the order Thysanoptera, for example, Frankliniella spp., Hercinothrips spp., Taeniothrips spp., *Thrips palmi, Thrips tabaci* and *Scirtothrips aurantii*;

from the order Heteroptera, for example, Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.;

from the order Homoptera, for example, *Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma lanigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Scnizaphis spp., Sitobion spp., *Trialeurodes vaporariorum, Trioza erytreae* and *Unaspis citri*;

from the order Hymenoptera, for example, Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order Diptera, for example, Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

from the order Siphonaptera, for example, Ceratophyllus spp. and *Xenopsylla cheopis*;

from the order Thysanura, for example, *Lepisma saccharina* and from the order Acarina, for example, *Acarus siro, Aceria sheldoni*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., Phyllocoptruta spp., Polyphagotarsonemus spp., Psoroptes spp., Rhipicephalus spp., Rhizoglyphus spp., Sarcoptes spp., Tarsonemus spp. and Tetranychus spp.

Especially representatives of the order Acarina can be controlled within the scope of the subject of the invention. These include, in particular, Aculus spp., in particular *A. schlechtendali*; Brevipalpus spp., in particular *B. californicus* and *B. phoenicis*; Phyllocoptruta spp., in particular *P. oleivora*; Eriophyes spp., in particular *E. vitis*; Panonychus spp., in particular *P. ulmi* and *P. citri*; Eotetranychus spp., in particular *E. carpini* and *E. orientalis*; Polyphagotarsonemus spp., in particular *P. latus*; and Tetranychus spp., in particular *T. urticae, T. cinnabarinus* and *T. kanzawai*.

The active ingredient mixtures according to the invention allow pests of the abovementioned type which are found in particular on plants, especially on useful plants and ornamentals in agriculture, in horticulture and in forests, or on the organs of such plants, such as fruits, flowers, foliage, stalks, tubers or roots, to be controlled, i.e. contained or destroyed, even plant organs which grow at a later point in time in some cases being protected against these pests.

The active ingredient mixtures according to the invention can be employed advantageously for controlling pests in rice, cereals, such as maize or sorghum; in fruit, e.g. pome fruit, stone fruit and soft fruit, such as apples, pears, plums, peaches, almonds, cherries and berries, e.g. strawberries, raspberries and blackberries; in leguminous plants, such as beans, lentils, peas and soya; in oil crops, such as oil seed rape, mustard, poppies, olives, sunflowers, coconuts, castor, cocoa and peanuts; in cucurbits, such as pumpkins, cucumbers and melons; in fibre plants, such as cotton, flax, hemp and jute; in citrus fruit, such as oranges, lemons, grapefruits and tangerines; in vegetables, such as spinach, lettuce, asparagus, cabbages, carrots, onions, tomatoes, potatoes and bell peppers; in representatives of the laurel family, such as avocado, cinnamonium and camphor; or in tobacco, nuts, coffee, eggplants, sugar cane, tea, pepper, grape vines, hops, the plantain family, latex plants or ornamentals, especially in rice, maize, sorghum, pome and stone fruit, leguminous plants, cucurbits, cotton, citrus fruit, vegetables, eggplants, grape vines, hops or ornamentals, in particular in maize, sorghum, apples, pears, plums, peaches, beans, peas, soya, olives, sunflowers, coconuts, cocoa, peanuts, cucumbers, pumpkins, citrus fruit, cabbages, tomatoes, potatoes, grape vines or cotton, especially preferably in rice, grape vines, citrus fruit, apples, pears, tomatoes and cotton, very especially preferably in rice.

Other fields of application for the active ingredient mixtures according to the invention are the protection of stored products and stores and of materials and, in the hygene sector, in particular the protection of domestic animals and productive livestock against pests of the abovementioned type.

Depending on the intended aims and prevailing circumstances, the pesticides according to the invention are emulsifiable concentrates, suspension concentrates, directly sprayable or dilutable solutions, spreadable pastes, dilute emulsions, sprayable powders, soluble powders, dispersible powders, wettable powders, dusts, granules or encapsulations in polymeric substances, all of which comprise the compound of the formula (A) and the active ingredient (B).

In these compositions, the active ingredients are employed together with at least one of the auxiliaries conventionally used in the art of formulation, such as extenders, e.g. solvents or solid carriers, or such as surface-active compounds (surfactants). Suitable solvents, solid carriers, surface-active compounds, non-ionic surfactants, cationic surfactants and anionic surfactants are for instance the same as mentioned in EP-A-736252.

As a rule, the compositions comprise 0.1 to 99%, in particular 0.1 to 95%, of a mixture of the active ingredient of the formula (A) with the active ingredient of the formula (B), and 1 to 99.9%, in particular 5 to 99.9%, of—at least—one solid or liquid auxiliary, it being possible for the surfactants to amount to, as a rule, 0 to 25%, in particular 0.1 to 20%, of the corn positions (% means in each case per cent by weight). While concentrated compositions are more preferred as commercially available goods, the end users uses, as a rule, dilute compositions which have considerably lower concentrations of active ingredient. Preferred compositions are, in particular, composed as follows (%=percent by weight):

Emulsifiable concentrates:

| | |
|---|---|
| Mixture of (A) and (B): | 1 to 90%, preferably 5 to 20% |
| Surfactant: | 1 to 30%, preferably 10 to 20% |
| Solvent: | 5 to 98%, preferably 70 to 85% |

Dusts:

| | |
|---|---|
| Mixture of (A) and (B): | 0.1 to 10%, preferably 0.1 to 1% |
| Solid carrier: | 99.9 to 90%, preferably 99.9 to 99% |

Suspension concentrates:

| | |
|---|---|
| Mixture of (A) and (B): | 5 to 75%, preferably 10 to 50% |

-continued

| | |
|---|---|
| Water: | 94 to 24%, preferably 88 to 30% |
| Surfactant: | 1 to 40%, preferably 2 to 30% |

Wettable powders:

| | |
|---|---|
| Mixture of (A) and (B): | 0.5 to 90%, preferably 1 to 80% |
| Surfactant: | 0.5 to 20%, preferably 1 to 15% |
| Solid carrier | 5 to 99%, preferably 15 to 98% |

Granules:

| | |
|---|---|
| Mixture of (A) and (B): | 0.5 to 30%, preferably 3 to 15% |
| Solid carrier: | 99.5 to 70%, preferably 97 to 85% |

The compositions according to the invention may also comprise further solid or liquid auxiliaries, such as stabilizers, e.g. epoxidized or unepoxidized vegetable oils (e.g. epoxidized coconut oil, rape seed oil or soya oil), antifoams, e.g. silicone oil, preservatives, viscosity regulators, binders and/or tackifiers, and also fertilizers or other active ingredients for achieving specific effects, e.g. bactericides, fungicides, nematicides, molluscicides or herbicides.

The compositions according to the invention are prepared in a known manner, e.g. prior to mixing with the auxiliary (auxiliaries) by grinding, screening and/or compressing an active ingredient or the active ingredient mixture, e.g. to give a specific particle size, and also by intimately mixing and/or grinding the active ingredient mixture with the auxiliary (auxiliaries). The invention therefore also relates to the process for the preparation of the compositions.

The invention furthermore relates to the methods of application for the compositions, i.e. the methods for controlling pests of the abovementioned type, such as spraying, wetting, atomizing, dusting, brushing on, seed dressing, scattering or pouring, which are to be selected to suit the intended aims and the prevailing circumstances, and to the use of the compositions for controlling pests of the abovementioned type. Typical rates of concentration are between 0.1 and 1000 ppm, preferably between 0.1 and 500 ppm, of active ingredient. The rate of application can be varied within wide ranges and depends on the consistency of the soil, the type of application (foliar application; seed dressing; use in the seed furrow), the crop plant, the pest to be controlled, the climatic circumstances which prevail in each case, and other factors determined by type of application, application timing and target crop. The rates of application per hectare are generally 1 to 2000 g of active ingredient mixture per hectare, in particular 10 to 1000 g/ha, preferably 20 to 600 g/ha, especially preferably 20 to 200 g/ha.

A preferred method of application in the field of crop protection is application to the foliage of the plants (foliar application), the frequency and rate of application depending on the danger of infestation with the pest in question. Alternatively, the active ingredients may reach the plants through the root system (systemic action), by drenching the locus of the plant with a liquid composition or by incorporating the active ingredients in solid form into the locus of the plants, e.g. into the soil, for example in the form of granules (soil application). In the case of paddy rice, such granules may be metered into the flooded paddy field.

The compositions according to the invention are also suitable for protecting plant propagation material, e.g. seed, such as fruits, tubers or kernels, or nursery plants, against animal pests. The propagation material can be treated with the composition prior to planting, for example seed may be dressed prior to sowing. Alternatively, the active ingredients according to the invention can be applied to seed kernels (coating), either by soaking the kernels in a liquid composition or by coating them with a solid composition. Alternatively, the composition may be applied to the site of application when the propagation material is planted, for example into the seed furrow in the case of sowing. The invention furthermore relates to these treatment methods for plant propagation material and to the plant propagation material thus treated.

The examples which follow are intended to illustrate the invention. They do not limit the invention.

FORMULATION EXAMPLES (%=Percent By Weight, Ratios of Active Ingredients=Weight Ratios)

| Example F1: Emulsion concentrates | a) | b) | c) |
|---|---|---|---|
| Active ingredient mixture [ratio of the compound of the formula (A) to the compound of the formula (B): 2:5] | 25% | 40% | 50% |
| Calcium dodecylbenzenesulfonate | 5% | 8% | 6% |
| Castor oil polyethylene glycol ether (36 mol of EO) | 5% | — | — |
| Tributylphenyl polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by diluting them with water.

| Example F2: Solutions | a) | b) | c) | d) |
|---|---|---|---|---|
| Active ingredient mixture (A:B = 150:1) | 80% | 10% | 5% | 95% |
| Ethylene glycol monomethyl ether | 20% | — | — | — |
| Polyethylene glycol MW 400 | — | 70% | — | — |
| N-methyl-2-pyrrolidone | — | 20% | — | — |
| Epoxidized coconut oil | — | — | 1% | 5% |
| Petroleum ether (boiling range 160–190° C.) | — | — | 94% | — |

The solutions are suitable for use in the form of microdrops.

| Example F3: Granules | a) | b) | c) | d) |
|---|---|---|---|---|
| Active ingredient mixture (A:B = 2:5) | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredients are dissolved together in dichloromethane, the solution is sprayed onto the carrier and the solvent is subsequently evaporated in vacuo.

| Example F4: Dusts | a) | b) |
|---|---|---|
| Active ingredient mixture (A:B = 4:1) | 2% | 5% |
| Highly disperse silica | 1% | 5% |
| Talc | 97% | — |
| Kaolin | — | 90% |

Ready-to-use dusts are obtained by intimately mixing the carriers with the active ingredients.

| Example F5: Wettable powders | a) | b) | c) |
|---|---|---|---|
| Active ingredient mixture (A:B = 5:3) | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenyl polyethylene glycol ether (7–8 mol of EO) | — | 2% | — |
| Highly disperse silica | 5% | 10% | 10% |
| Kaolin | 62% | 27% | — |

The active ingredients are mixed with the additives and ground thoroughly in a suitable mill. This gives wettable powders which can be diluted with water to give suspensions of any desired concentration.

| Example F6: Emulsion concentrate | |
|---|---|
| Active ingredient mixture (150:1) | 10% |
| Octylphenyl polyethylene glycol ether (4–5 mol of EO) | 3% |
| Calcium dodecylbenzenesulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by diluting it with water.

| Example F7: Dusts | a) | b) |
|---|---|---|
| Active ingredient mixture (6:1) | 5% | 8% |
| Talc | 95% | — |
| Kaolin | — | 92% |

Ready-to-use dusts are obtained by mixing the active ingredients with the carrier and grinding the mixture in a suitable mill.

| Example F8: Extruder granules | |
|---|---|
| Active ingredient mixture (3:1) | 10% |
| Sodium lignosulfonate | 2% |
| Carboxymethylcellulose | 1% |
| Kaolin | 87% |

The active ingredients are mixed with the additives, and the mixture is ground and moistened with water. This mixture is extruded, granulated and subsequently dried in a stream of air.

| Example F9: Coated granules | |
|---|---|
| Active ingredient mixture (4:1) | 3% |
| Polyethylene glycol (MW200) | 3% |
| Kaolin | 94% |

In a mixer, the finely ground active ingredients are applied uniformly to the kaolin which has been moistened with polyethylene glycol. This gives dust-free coated granules.

| Example F10: Suspension concentrate | |
| --- | --- |
| Active ingredient mixture (150:1) | 40% |
| Ethylene glycol | 10% |
| Nonylphenyl polyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredients are mixed intimately with the additives. This gives a suspension concentrate from which suspensions of any desired concentration can be prepared by diluting with water.

Frequently, it is more convenient to formulate the active ingredient of the formula (A) and the component (B) individually and then to combine them in the applicator in the desired mixing ratio in water as a "tank mix" shortly before application.

BIOLOGICAL EXAMPLES

%=Percent by Weight Unless Otherwise Specified

A pesticidally synergistic effect is always present when the activity of the combination of the active ingredient of the formula (A) with the active ingredient of the formula (B) exceeds the total of the activities of the active ingredients when applied individually.

$$EA_1 > X+Y \qquad (I)$$

The expected pesticidal action $EA_2$ for a given combination of two pesticides can, however, also be calculated as follows (cf. COLBY, S. R., "Calculating synergistic and antagonistic response of herbicide combinations", Weeds 15, pages 20–22, 1967):

$$EA_2 = X + \frac{Y(100-X)}{100} \qquad (II)$$

In this formula,

X=percent mortality when treated with the compound of the formula (A) at a rate of application of p kg per hectare in comparison with the untreated control (=0%).

Y=percent mortality when treated with the compound of the formula (B) at a rate of application of q kg per hectare in comparison with the untreated control.

$EA_1$, $EA_2$=expected pesticidal activity (percent mortality in comparison with untreated control) after treatment with the compound of the formula (A) and the compound of the formula (B) at a rate of application of p+q kg of active ingredient per hectare.

If the actually observed activity exceeds the expected value $EA_1$ or $EA_2$, synergism is present.

The synergistic effect of the combinations of the active ingredient of the formula (A) with the active ingredient of the formula (B) is demonstrated in the examples which follow.

Example B1

Activity Against *Bemisia tabaci*

Dwarf bean plants are placed into gauze cages and populated with adult *Bemisia tabaci*. After oviposition has taken place, all adults are removed. 10 days later, the plants together with the nymphs thereon are sprayed with an aqueous suspension spray mixture comprising 50 ppm of active ingredient mixture. After a further 14 days, the hatching rate of the eggs is evaluated in percent in comparison with untreated control batches.

In this test, the combinations of the active ingredient of the formula (A) with the active ingredient of the formula (B) have a synergistic effect. In particular, the combination of the active ingredient of the formula (A) with the active ingredient of the formula (B) in a ratio of 150:1 and in a ratio of 2:5 has an activity of over 80%.

Example B2

Activity Against *Spodoptera littoralis* Caterpillars

Young soya plants are sprayed with an aqueous emulsion spray mixture comprising 400 ppm of the active ingredient mixture. After the spray coating has dried on, the soya plants are populated with 10 third-instar caterpillars of *Spodoptera littoralis* and placed into a plastic container. The test is evaluated 3 days later. The reduction in population, or the reduction in feeding damage, is determined in percent (% activity) by comparing the number of dead caterpillars and the feeding damage on the treated plants with those on the untreated plants.

In this test, the combinations of the active ingredient of the formula (A) with the active ingredient of the formula (B) have a synergistic effect. In particular, the combination of the active ingredient of the formula (A) with the active ingredient of the formula (B) in a ratio of 4:1 and in a ratio of 2:1 has an activity of over 80%.

Example B3

Ovicidal Activity Against *Lobesia botrana*

*Lobesia botrana* eggs which have been deposited on filter paper are briefly immersed into a test solution comprising 400 ppm of the active ingredient mixture to be tested in acetone/water. After the test solution has dried on, the eggs are incubated in Petri dishes. After 6 days, the hatching rate of the eggs is evaluated in percent in comparison with untreated control batches (% reduction in hatching rate).

In this test, the combinations of the active ingredient of the formula (A) with the active ingredient of the formula (B) have a synergistic effect. In particular, the combination of the active ingredient of the formula (A) with the active ingredient of the formula (B) in a ratio of 4:1 and in a ratio of 2:5 has an activity of over 80%.

Example B4

Activity Against *Panonychus ulmi* (OP- and Carb.-Resistant)

Apple seedlings are populated with adult female *Panonychus ulmi*. After seven days, the infected plants are sprayed until dripping wet with an aqueous emulsion spray mixture comprising 400 ppm of the compound to be tested and grown in the greenhouse. After 14 days, the test is evaluated. The reduction in population is determined in percent (% activity) by comparing the number of dead spider mites on the treated plants with those on the untreated plants.

In this test, the combinations of the active ingredient of the formula (A) with the active ingredient of the formula (B) have a synergistic effect. In particular, the combination of the active ingredient of the formula (A) with the active ingredient of the formula (B) in a ratio of 2:5, 4:1 and 1:2 has an activity of over 80%.

Example B5

Activity Against *Tetranychus urticae*

Young bean plants are populated with a mixed population of *Tetranychus urticae* and 1 day later sprayed with an aqueous emulsion spray mixture comprising 400 ppm of the active ingredient. The plants are subsequently incubated for 11 days at 24° C. and then evaluated. The reduction in population is determined in percent (% activity) by comparing the number of dead eggs, larvae and adults on the treated plants with those on the untreated plants.

In this test, the combinations of the active ingredient of the formula (A) with the active ingredient of the formula (B) have a synergistic effect. In particular, the combination of the active ingredient of the formula (A) with the active ingredient of the formula (B) in a ratio of 3:5, 1:2 and 1:1 are very effective.

What is claimed is:

1. A pesticidal composition which comprises, in variable quantities, a pesticidally active compound of the formula

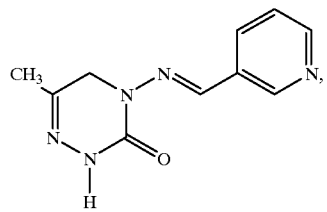

(A, pymetrozine)

in free form or in the form of an agrochemically acceptable salt thereof,
and a pesticidally active compound of the formula

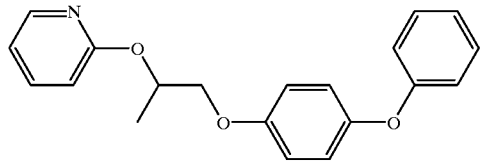

(B, pyriproxyfen)

in free form or in the form of an agrochemically acceptable salt thereof, and at least one auxilliary
wherein compounds A and B are present in a synergistic ratio of compound A to compound B,
said ratio of compound A to compound B is at least 1:200, and
said ratio of compound A to compound B being not greater than 200:1, and the total concentration of compound A and compound B in said composition is at least a combined amount of 0.1 ppm.

2. The composition according to claim 1 which comprises, as active ingredients, the compounds of the formula (A) and of the formula (B) in free form.

3. A process for the preparation of a composition according to claim 1 comprising intimately mixing compounds (A) and (B) with said at least one auxilliary.

4. A composition which comprises, in variable quantities, a pesticidally active compound of the formula

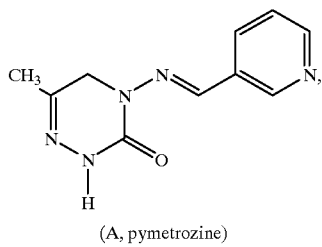

(A, pymetrozine)

in free form in the form of an agrochemically acceptable salt thereof,
and a pesticidally active compound of the formula

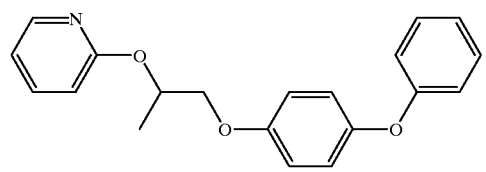

(B, pyriproxyfen)

in free form or in the form of an agrochemically acceptable salt thereof
wherein compounds A and B are present in a synergistic ratio of compound A to compound B,
said ratio of compound A to compound B is at least 1:200, and
said ratio of compound A to compound B being not greater than 200:1.

5. A method of controlling pests, which comprises applying a composition as described in claim 1 to the pests or to their environment wherein said composition is applied at a rate of at least 1 g per hectacre, and said composition is applied in an amount of not more than 2000, g per hectacre, said application rates being based on amount of active agent.

6. The method according to claim 5 wherein said pests are from the order Acarina.

7. The method as claimed in claim 5 wherein said applying is step is applying said composition to plant propagation material or the locus of planting of said plant propagation material.

8. Plant propagation material treated according to the method described in claim 7.

* * * * *